(12) United States Patent
Moody et al.

(10) Patent No.: US 8,703,945 B2
(45) Date of Patent: Apr. 22, 2014

(54) PROCESS AND INTERMEDIATE COMPOUNDS USEFUL IN THE PREPARATION OF STATINS, PARTICULARLY ROSUVASTATIN

(75) Inventors: David J. Moody, Fife (GB); Jonathan W. Wiffen, Craigavon (GB)

(73) Assignee: Redx Pharma Limited, Manchester (GB)

( * ) Notice: Subject to any disclaimer, the term of this patent is extended or adjusted under 35 U.S.C. 154(b) by 1068 days.

(21) Appl. No.: 10/594,380

(22) PCT Filed: Mar. 23, 2005

(86) PCT No.: PCT/GB2005/001099
§ 371 (c)(1),
(2), (4) Date: Jul. 29, 2008

(87) PCT Pub. No.: WO2005/092867
PCT Pub. Date: Oct. 6, 2005

(65) Prior Publication Data
US 2008/0281101 A1    Nov. 13, 2008

(30) Foreign Application Priority Data
Mar. 26, 2004  (GB) .................................. 0406757.5

(51) Int. Cl.
*C07D 239/42*       (2006.01)
*C07D 403/12*       (2006.01)

(52) U.S. Cl.
USPC ........................................................ 544/330

(58) Field of Classification Search
USPC ........................................................ 544/330
See application file for complete search history.

(56) References Cited

U.S. PATENT DOCUMENTS

| 4,474,971 A | 10/1984 | Wareing |
| 4,625,039 A | 11/1986 | Jewell, Jr. et al. |

(Continued)

FOREIGN PATENT DOCUMENTS

| DE | WO 2005/047276 A2 | 5/2005 |
| WO | WO-01/85702 A1 | 11/2001 |

(Continued)

OTHER PUBLICATIONS

Wade et al. J. Org. Chem. 59:7199-7200 (1994).*

(Continued)

*Primary Examiner* — Venkataraman Balasubramanian
(74) *Attorney, Agent, or Firm* — Alan W. Steele; Foley Hoag LLP

(57) ABSTRACT

There is provided a process for the preparation of a compound of formula (7) wherein $R^1$ represents an alkyl group; $R^2$ represents an aryl group; $R^3$ represents hydrogen, a protecting group or an alkyl group; and $R^4$ represents hydrogen, a protecting group or a $SO_2R^5$ group where $R^5$ is an alkyl group, which comprises a) hydroxylating a compound of formula (1) wherein Y represents a halo group; $P^1$ represents hydrogen or a protecting group, and W represents =O or —$OP^2$, in which $P^2$ represents hydrogen or a protecting group, to give a compound of formula (2), b) oxidixing the compound of formula (2) to give a compound of formula (3), c) coupling the compound of formula (3) with a compound of formula (4), wherein $R^3$ represents a protecting group or an alkyl group; $R^4$ represents a protecting group or a $SO_2R^5$ group where $R^5$ is an alkyl group; and $R^6$ represents $(PR^7R^8)+X^-$ or $P(=O)R^7R^8$ in which X is an anion and $R^7$ and $R^8$ each independently is an alkyl, aryl.

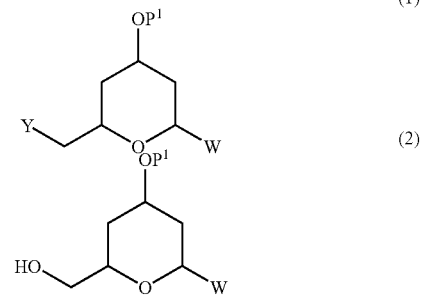

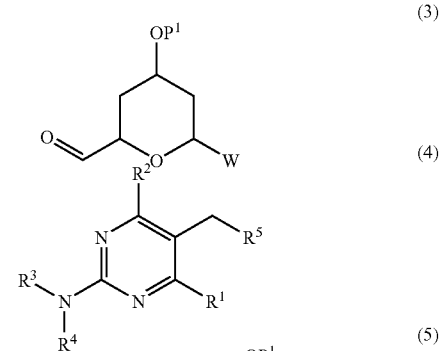

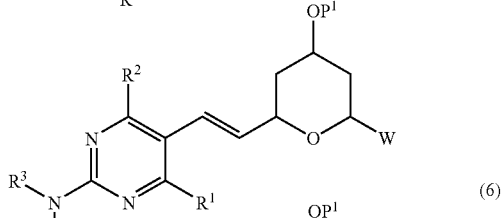

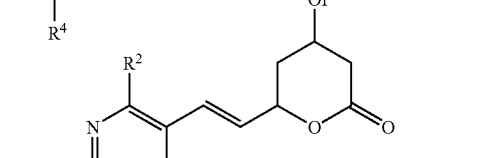

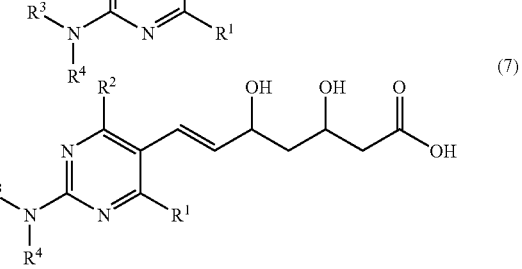

12 Claims, No Drawings

(56) References Cited

U.S. PATENT DOCUMENTS

| | | |
|---|---|---|
| 4,677,211 A | 6/1987 | Jewell, Jr. et al. |
| 2003/0232989 A1 | 12/2003 | Antons et al. |
| 2004/0006097 A1* | 1/2004 | Hill et al. .................. 514/275 |

FOREIGN PATENT DOCUMENTS

| | | |
|---|---|---|
| WO | WO-03/026573 A2 | 4/2003 |
| WO | WO-2005/030758 A1 | 4/2005 |
| WO | WO-2005/040134 A1 | 5/2005 |

OTHER PUBLICATIONS

Barth, M. et al., "Towards a New Type of HMG-CoA Reductase Inhibitor", *Tetrahedron*, 46(19):6731-6740 (Elsevier Science Publishers, Amsterdam, NL, 1990).

Beck, G. et al., "Synthesis and Biological Activity of New HMG-CoA Reductase Inhibitors. 1. Lactones of Pyridine- and Pyrimidine-Substituted 3,5-Dihydroxy-6-heptenoic(-heptanoic) Acids", *J. Med. Chem.*, 33(1):52-60 (American Chemical Society, Washington, DC, 1990).

Durand-Reville, T. et al., "Highly Selective Entry to the Azadirachtin Skeleton via a Claisen Rearrangement/Radical Cyclization Sequence", *Organic Letters*, 4(22):3847-3850 (2002).

Paterson, I. et al., "Phorboxazole B synthetic studies: construction of C(1-32) and C(33-46) subtargets", *Organic & Biomolecular Chemistry*, 2(20):3026-3038 (2004).

Rosen, T. et al., "Synthetic and Biological Studies of Compactin and Related Compounds. 2. Synthesis of the Lactone Moiety of Compactin", *J. Org. Chem.*, 49:3994-4003 (American Chemical Society, Easton, US, Oct. 19, 1994).

Yang, Y.-L. et al., "Mevinic Acids and Analogues: Preparatrion of a Key Chiral Intermediate", *Tetrahedron Letters*, 23(42):4305-4308 (Pergamon Press Ltd., Great Britain, 1982).

International Search Report dated Sep. 16, 2005.

Barnes, N.J. et al., "The Synthesis of Optically Active Tetrahydropyrans by the Addition of a Stabilised Wittig Reagent to Pyranose Sugars," J. Chem. Soc., Chem. Commun., (19):1292-1294 (1985).

Wiberg K.B. et al., "Lactones. 3. A Comparison of the Basicities of Lactones and Esters," *J. Am. Chem. Soc.* 113:7705-7709 (1991).

"Chapter 27. Reactions of Enolates with Aldehydes and Ketones: the Aldol Reaction," *Organic Chemistry*, eds. Clayden, Greeves, Warren, and Wothers, Oxford University Press, 2001, pp. 692-693.

"Chapter 28. Acylation at Carbon", *Organic Chemistry*, eds. Clayden, Greeves, Warren, and Wothers, Oxford University Press, 2001, pp. 723-724.

\* cited by examiner

PROCESS AND INTERMEDIATE COMPOUNDS USEFUL IN THE PREPARATION OF STATINS, PARTICULARLY ROSUVASTATIN

RELATED APPLICATIONS

This application claims the benefit of priority to Patent Cooperation Treaty Application number PCT/GB2005/001099, filed Mar. 23, 2005; which claims the benefit of priority to Great Britain Patent Application serial number 0406757.5, filed Mar. 26, 2004. The entirety of both of them is hereby incorporated by reference.

The present invention concerns a process and intermediate compounds useful in the preparation of statins, particularly Rosuvastatin.

According to the present invention, there is provided a process for the preparation of a compound of formula (7):

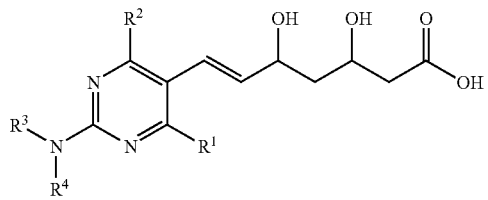

wherein
- $R^1$ represents an alkyl group, such as a $C_{1-6}$ alkyl group, and preferably an isopropyl group;
- $R^2$ represents an aryl group, preferably a 4-fluorophenyl group;
- $R^3$ represents hydrogen, a protecting group or an alkyl group, such as a $C_{1-6}$ alkyl group, and preferably a methyl group; and
- $R^4$ represents hydrogen, a protecting group or a $SO_2R^5$ group where $R^5$ is an alkyl group, such as a $C_{1-6}$ alkyl group, and preferably a methyl group, which comprises a) hydroxylating a compound of formula (1):

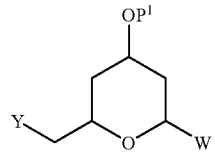

wherein Y represents a halo group, preferably Cl or Br; $P^1$ represents hydrogen or a protecting group, and W represents =O or —$OP^2$, in which $P^2$ represents hydrogen or a protecting group, to give a compound of formula (2):

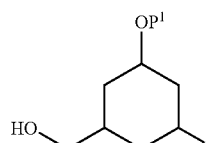

b) oxidising the compound of formula (2) to give a compound of formula (3):

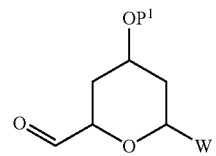

c) coupling the compound of formula (3) with a compound of formula (4):

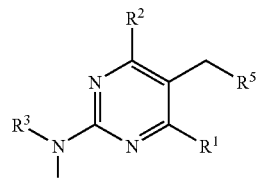

wherein $R^3$ represents a protecting group or an alkyl group, such as a $C_{1-8}$ alkyl group, and preferably a methyl group; $R^4$ represents a protecting group or a $SO_2R^5$ group where $R^5$ is an alkyl group, such as a $C_{1-6}$ alkyl group, and preferably a methyl group; and $R^6$ represents $(PR^7R^8)^+X^-$ or $P(=O)R^7R^8$ in which X is an anion and $R^7$ and $R^8$ each independently is an alkyl, aryl, alkoxy or aryloxy group, preferably a phenyl group, to give a compound of formula (5):

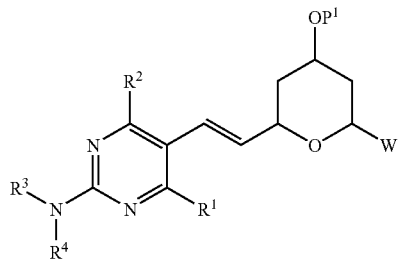

wherein $R^3$ represents a protecting group or an alkyl group, such as a $C_{1-6}$ alkyl group, and preferably a methyl group; and $R^4$ represents a protecting group or a $SO_2R^5$ group where $R^5$ is an alkyl group, such as a $C_{1-6}$ alkyl group, and preferably a methyl group, d) when W represents —$OP^2$, removing any $P^2$ protecting group and oxidising the compound of formula (5) to give a compound of formula (6):

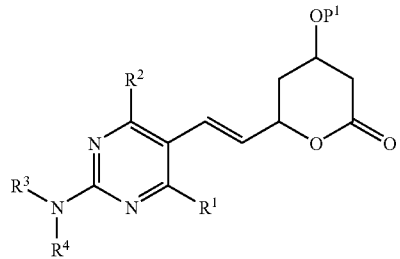

and e) subjecting the compound of formula (5) when W represents =O, or compound of formula (6) to ring-opening, removal of any P¹ protecting groups, and optionally removing any additional protecting groups to give a compound of formula (7).

In step (e), any P¹ protecting groups and any additional protecting groups may be removed individually or together and prior to ring opening, during ring opening or after ring opening of the compounds of formula (5) or (6).

Preferably, in steps (a) to (c), W is OP² for the compounds of formula (1), (2), (3) and (5).

Protecting groups which may be represented by P¹ and P² include alcohol protecting groups, examples of which are well known in the art. Particular examples include tetrahydropyranyl, benzyl and methyl groups, and optionally substituted variants thereof. Substituents may advantageously be used to modify the ease of introduction or removal of the protecting group. Preferred protecting groups are silyl groups, for example triaryl- and especially trialkylsilyl groups. Especially preferred examples are trimethylsilyl, t-butyldimethylsilyl and t-butyldiphenylsilyl groups.

Protecting groups which may be represented by P¹ and P² may be the same or different. When the protecting groups P¹ and P² are different, advantageously this may allow for the selective removal of only P¹ or P². Preferably, when the protecting groups P¹ and P² are different, P¹ is a tetrahydropyranyl, benzyl, or silyl group and P² is a methyl group. More preferably, when the protecting groups P¹ and P² are different, P¹ is a benzyl, or silyl group and P² is a methyl group.

Protecting groups which may be represented by R³ and R⁴ include amine protecting groups, examples of which are well known in the art. Particular examples include benzyl groups, carbamates (such as CBZ, Boc, Fmoc), phosphate, thiophosphate, silyl groups and, when R³ and R⁴ together are a single protecting group, an imine group.

Hyrdoxylation of compounds of formula (1) can be achieved by methods known in the art for displacing a halo group with a hydroxide source. Preferably, the process comprises contacting the compound of formula (1) with a source of hydroxide. Hydroxide sources include hydroxide salts, especially ammonium or alkali metal hydroxides, particularly lithium, sodium or potassium hydroxide, and various aqueous media such as water in the presence of basic media such as N-methylpryrrolidinone, HMPA, $Al_2O_3$, $CaCO_3$, $Na_2CO_3$, $K_2CO_3$ or $KO_2$/18-crown-6, silver salts such as $AgNO_3$ or $Ag_2O$, or oxidants such perbenzioc acid. A particularly preferred process comprises contacting the compound of formula (1) with 5 molar equivalents of KOH in the presence of dimethylsulfoxide solvent at a temperature of, for example, about 50° C.

Alternatively, hydroxylation may be achieved by first displacing the halogen with a leaving group such as acetate, triflate or sulphate optionally In the presence of a silver salt, then displacing the leaving group with a hydroxide source. A particularly preferred process comprises contacting the compound of formula (1) with 3 molar equivalents of NaOAc in the presence of dimethylformamide solvent and tetra-n-butylammonium chloride at a temperature of, for example, about 100° C., isolating the acetyl compound and contacting with potassium carbonate in the presence of methanol solvent and at a temperature of, for example, about 0° C.

Oxidation of compounds of formula (2) can be achieved using oxidation systems known in the art for the oxidation of alcohols, especially those known in the art for the oxidation of primary alcohols. Examples include oxidation with Dess-Martin periodinane, bromine, Swern oxidation or various metal based oxidations such as Fetizon reagent, manganate based reagents, and chromate based reagents such as Collins reagent. Swern oxidation is preferred. When Swern oxidation is employed, preferred conditions comprise the use of dimethyl sulphoxide and oxalyl chloride or bromine in a solvent such as dichloromethane or dichlormethane/THF mixtures, at reduced temperature, such as from 0 to −100° C., preferably −50 to −80° C. Preferably, reagents are added at reduced temperature, such as −30 to −80° C., and then once all reagents are added, the reaction mixture is allowed to warm to 15 to 20° C.

Alternatively, the compound of formula (3) may be obtained directly from a compound of formula (1), for example by treatment with dimethysulphoxide and an acid acceptor.

The coupling of the compound of formula (3) with the compound of formula (4) may employ conditions analogous to those given in WO01/85702 for the corresponding coupling of a compound of formula (4). Alternatively, conditions comprising refluxing the compounds of formula (3) and (4) in a hydrocarbon solvent, such as toluene or cyclohexane, or mixtures thereof, followed by contact with aqueous acid, such as aqueous HCl may be employed.

Alkyl, aryl, alkoxy or aryloxy groups which may be represented by R⁷ and R⁸ include $C_{1-6}$alkyl groups, such as methyl and ethyl groups, $C_{6-12}$aryl groups, such phenyl, tolyl or naphthyl, $C_{1-6}$alkoy groups, such as ethoxy groups, and $C_{8-12}$aryloxy groups such as phenoxy groups.

Anions which may be represented by X include halide.

R⁶ preferably is P(=O)R⁷R⁸ where R⁷ and R⁸ each independently is an alkyl, aryl, alkoxy or aryloxy group, preferably a phenyl group.

When W represents OP², the protecting group may be removed to form a hydroxy group by methods known in the art for the removal of the given protecting group. For example, silyl protecting groups may be removed by contact with a source of fluoride ion, such as tetrabutylammonium fluoride.

Oxidation of compounds formed by deprotection of compounds wherein W represents —OP² may employ conditions known in the art for the oxidation of pyranols to pyranones, and include those given in "Comprehensive Organic Transformations", R. C. Larock, $2^{nd}$ Ed (1999) p 1670, published by Wiley VCH, incorporated herein by reference. Preferred oxidation systems include $Ag_2CO_3$/Celite, especially Celite J2, bromine or Swern.

Ring opening of the compounds of formula (5), when W represent =O or formula (6) may employ conditions known in the art for ring opening of a pyranone. Preferably, the ring is opened by contact with a base, such as sodium hydroxide or calcium oxide. Conveniently, polar solvents are employed, for example methanol, acetonitrile, tetrahydrofuran or mixtures thereof.

Remaining protecting groups may be removed by methods known in the art for the removal of the given protecting group. For example, silyl protecting groups may be removed by contact with a source of fluoride ion, such as tetrabutylammonium fluoride, and benzyl groups may be removed by treatment with TMSI or under selective hydrogenation conditions.

It will also be recognised that compounds of formulae (2), (3) and (5) may also be subjected to oxidation (when W represents —OH) or deprotection and oxidation (when W represents (—O-protecting group) to form the corresponding compound wherein W represents =O.

Preferred compounds of formula (1) are compounds of formula:

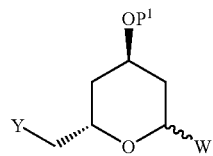

wherein W, $P^1$ and Y are as previously described.

Preferred compounds of formula (2) are compounds of formula:

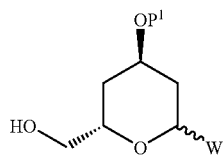

wherein W and $P^1$ are as previously described.

Preferred compounds of formula (3) are compounds of formula:

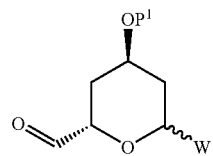

wherein W and $P^1$ are as previously described.

Preferred compounds of formula (5) are of formula:

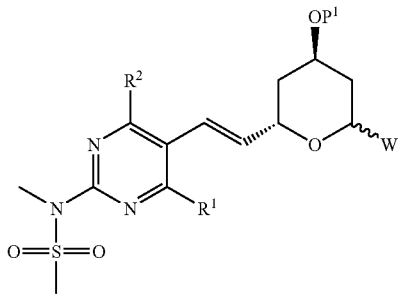

wherein $R^1$, $R^2$, W and $P^1$ are as previously described.

Preferred compounds of formula (6) are of formula:

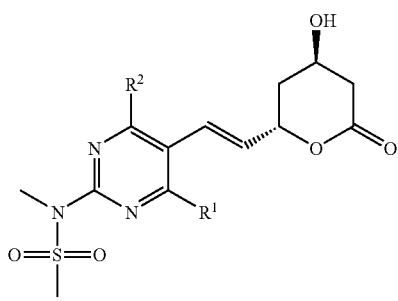

wherein $R^1$ and $R^2$ are as previously described.

Preferred compounds of formula (7) are of formula:

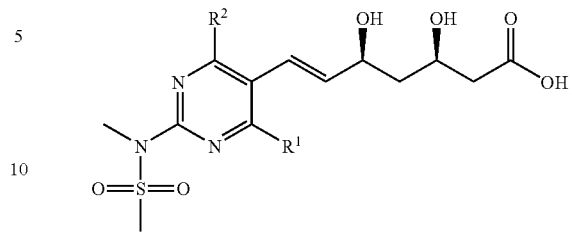

wherein $R^1$ and $R^2$ are as previously described.

Compounds of formula (7) are advantageously converted to pharmaceutically acceptable salts, especially their calcium salts (for example WO01160804).

Compounds of formula (4) are advantageously prepared by the methods given in WO00149014 and WO01185702. Particularly preferred compounds of formula (4) are compounds of formula:

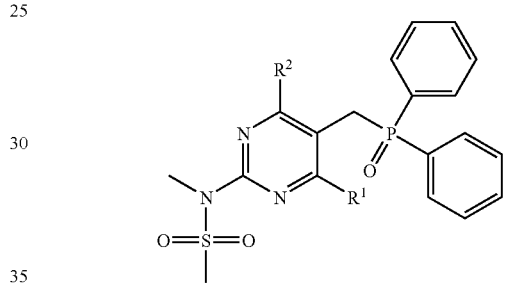

Compounds of formula (1) are advantageously prepared by enzyme catalysed condensation of acetaldehyde and 2-haloacetaldehyde, for example using the method given in U.S. Pat. No. 5,795,749.

Compounds of formulae (2) and (3) and, when W is $OP^2$, formula (5) form further aspects of the present Invention.

The invention is illustrated by the following examples.

EXAMPLE 1

Preparation of Chlorolactol Methyl Acetal ((2S,4R)-2-(chloromethyl)-6-methoxytetrahydro-2H-pyran-4-ol), a Compound of Formula 1 where Y=Cl, $P^1$=H and W=$OP^2$, in which $P^2$=Me Crude chlorolactol (15 g) was dissolved in methanol (150 ml) and heated to 40° C. for 2 hours in the presence of 0.1 ml sulphuric acid. The solvent was removed by rotary evaporation to afford the product as a dark brown flowing oil. The product was dissolved in DCM and washed with sodium bicarbonate solution. The solvent was removed by rotary evaporation to afford the product as a dark brown flowing oil, which was purified by column chromatography (16.1 g) containing a mixture of anomers m/z 179, 149 and 113; $^1$H nmr $CDCl_3$ 3.6-3.7 (m 2H), 4.1 (m 1H), 1.5-1.6 (m 2H), 4.0 (m 1H), 1.3-1.6 (m 2H), 4.9 (m 1H), 3.3 & 3.5 (s 3H); $^{13}$C nmr $CDCl_3$ 32, 36, 45, 55 & 56, 64, 65, 94.

EXAMPLE 2

Preparation of O-benzyl-chlorolactol Methyl Acetal ((2S,4R)-4-(benzyloxy)-2-(chloromethyl)-6-methoxytetrahydro-2H-pyran), a Compound of Formula 1 where Y=Cl, $P^1$=Bn and W=—$OP^2$, in which $P^2$=Me Chlorolactol methyl acetal (1 g) was dissolved in THF (5 ml) and charged to sodium hydride (0.33 g 60% in mineral oil) in THF (5 ml) at room temperature. Benzyl bromide (1.9 g) was added dropwise and the mass heated to 80° C. for 2 hours. Methanol (2 ml) was added and the mass was partitioned between DCM/water, and was then washed with water. The organic phase was dried and the solvent was removed by rotary evaporation to afford an orange flowing oil (2.1 g), containing a mixture of anomers containing a mixture of anomers. m/z 270; 238; 203; 132; 91; $^1$H nmr CDCl$_3$ 1.6-2.0 (m 4H), 3.4 & 3.5 (s 3H), 3.6 (m 2H), 3.8 (m 1H), 4.0 (m 1H), 4.5 (m 2H), 4.7 (m 1H), 7.3-7.5 (m 5H); $^{13}$C nmr CDCl$_3$ 32 & 33, 46, 55 & 56, 58, 66, 74, 96 & 98, 128-131.

EXAMPLE 3

Preparation of Hydroxy-O-benzyl-lactol Methyl Acetal ([(2R,4R)-4-(benzyloxy)-6-methoxytetrahydro-2H-pyran-2-yl]methanol), a Compound of Formula 2 where $P^1$=Bn and W=—$P^2$, in which $P^2$=Me Preparation of the Acetate Intermediate:

To a 3-liter three necked round bottomed flask flushed with dry nitrogen the O-benzyl-chlorolactol methyl acetal (30 g) was charged into dry N-methyl pyrollidinone (756 mls). Arihydrous tetrabutylammonium acetate (102.57 g) was also charged to the solution. The reaction mixture was then heated at 100° C. for 24 hours. The reaction mixture was sampled at routine intervals and directly analysed by tlc and gc/ms.

The black solution was then diluted with water (150 mls) and extracted with ethyl acetate (3×1500 mls). The combined upper organic layer was then washed with water (3×500 mls). The aqueous portion showed no product content at this point. The layers were then separated, dried, (Na$_2$SO$_4$) and the solvent removed in vacuo to yield a black flowing oil (31 g, 95%) containing a mixture of anomers. $^1$H nmr CDCl$_3$ 1.4-1.8 (m 4H), 2.0-2.1 (duplicate s, 3H), 3.4 & 3.5 (s 3H), 3.8 (m 1H), 4.0 (m 1H), 4.1 (m 2H), 4.5 (m, 2H), 4.7-4.9 (m 1H), 7.2-7.3 (m, 5H); $^{13}$C nmr CDCl$_3$ 20.8; 3q35; 55 & 56; 57 & 64; 66 & 68; 69 & 72; 70 & 71; 98 & 99; 127-128 & 138; 170.5; m/z 293, 262, 221, 203, 156, 91 and 43.

Preparation of the Alcohol from the Acetate Intermediate:

To a 50 mls three necked round bottomed flask flushed with dry nitrogen the O-benzyl-chlorolactol methyl acetal acetate (2 g) was charged into dry methanol (10 mls) containing anhydrous potassium carbonate (1 g). The resultant suspension was stirred at 20° C. for 30 minutes. G.C./M.S. showed complete conversion of acetate to alcohol. The solid was filtered off and the solvent removed in vacuo to yield a brown flowing oil containing a mixture of anomers (1.6 g, 93%). $^1$H nmr CDCl$_3$ 1.4-1.8 (m 4H), 3.4 & 3.5 (s 3H), 3.8 (m 1H), 3.9 (m 1H), 4.0 (m, 2H), 4.5 (m 2H), 4.7-4.9 (m, 5H); $^{13}$C nmr CDCl$_3$ 30-38; 55 & 56; 65 & 66; 65 & 69; 70 & 71; 72 & 73; 99&100; 128 & 140; m/z 252, 221, 189, 163, 114 and 91.

EXAMPLE 4

Preparation of formyl-O-benzyl-lactol Methyl Acetal (2S,4R)-4-(benzyloxy)-6-methoxytetrahydro-2H-pyran-2-carbaldehyde a Compound of Formula 3 where $P^1$=Bn and W=—$OP^2$, in which $P^2$=Me Dess-Martin periodinane reagent (1.91 g) in dichloromethane (50 mls) was charged to a 1000 mls round bottomed flask purged with dry nitrogen. The hydroxy-O-benzyl-lactol methyl acetal (1.0 g,) was dissolved in dichloromethane (50 mls) and added to the Dess-Martin periodinane reagent at 20° C. The reaction mixture was then stirred at room temperature for 30 minutes. The reaction was monitored by tlc. The reaction mixture was then diluted with diethyl ether (500 mls) to precipitate the excess reagent. The suspension was then washed with 10% aqueous sodium hydroxide (200 mls). The upper organic layer was then washed with water (250 mls). The upper organic layer was then separated, dried (Na$_2$SO$_4$) and the solvent removed in vacuo to yield a dark flowing oil as a mixture of anomers (0.8 g).

$^1$H nmr CDCl$_3$ 1.6-1.9 (m 4H), 3.3 & 3.5 (s 3H), 3.7 (m 1H), 3.8 (m 1H), 4.4 (m 2H), 4.7-4.9 (m 1H), 7.2-8.1 (m, 5H), 9.6-9.7 (2×s, 1H).

$^{13}$C nmr CDCl$_3$ 30-38; 55 & 56; 65 & 66; 65 & 69; 70 & 71; 99 & 100; 128 & 140; 201.

m/z 250, 221, 189, 163, 143, 117 and 91.

Alternatively, a Swern oxidation can be carried out as illustrated by the following example:

A stirred solution of oxalyl chloride (0.037 cm$^3$, 0.44 mmol) in dichloromethane (4 cm$^3$) under nitrogen was cooled to −78 C. and DMSO was added in one portion. A solution of the alcohol (100 mg, 0.40 mmol) in dichloromethane (1 cm$^3$) was added to the reaction mixture and the reaction mixture stirred at −78 C. for 5 min. Triethylamine (0.272 cm$^3$, 19.8 mmol) was added and the resulting solution was stirred at −78 C. for 25 min and used immediately without isolation or purification. Tlc r$_f$ 0.40 ethyl acetate:hexane (1:1) orange spot with 2,4-dinitrophenylhydrazine stain

EXAMPLE 5

Preparation of Pyrimidyl-ethenyl-O-benzyl-lactol Methyl Acetal, a Compound of Formula 5 where $R^1$=iPr, $R^2$=4-FC$_6$H$_4$, $R^3$=Me, $R^4$=SO$_2$Me, $P^1$=Bz and W=—$OP^2$, in which $P^2$=Me Pyrimidyl-ethenyl-O-benzyl-lactol methyl acetal was obtained by first dissolving 0.21 g of the compound of formula 4 wherein $R^3$=Me, $R^4$=SO$_2$Me and $R^6$=PO(Ph)$_2$ in 10 ml dry THF, cooling to −60° C. and then adding 0.2 ml of a 2M solution of sodium hexamethyldisilazide. After 20 min, a solution of 0.1 g formyl-O-benzyl-lactol methyl acetal in 10 ml dry THF at −30° C. was added. The reaction mixture was then maintained at this temperature for 8 hours and monitored by tlc. The reaction mixture was allowed to slowly warm up to 20° C. Glacial acetic (5 mls) acid was then charged to quench the reaction. Water (5 mls) was also charged to the mixture. The solvent was then removed in vacuo and reconstituted with toluene (15 mls) and water (15 mls). The upper organic layer was then separated and the aqueous layer was then washed with ethyl acetate (15 mls). The combined organics were then dried and the solvent removed in vacuo to yield an oil containing a mixture of isomers, that can be purified by chromatography. The desired product had the tentative NMR assignment ¹H nmr CDCl₃ 1.2 (d, 6H), 1.6-1.9 (m 4H), 3.3 (s, 3H), 3.4 (s, 3H), 3.2 & 3.5 (2×s, 3H), 3.7 (m 1H), 3.8 (m 1H), 4.2 (m 1H), 4.4 (m 2H), 4.7-4.9 (m 1H), 5.35 (dd, 1H), 5.85-6.7 (d, 1H), 7.1-8.1 (m, 9H).

EXAMPLE 6

Preparation of Pyrimidyl-ethenyl-OH-lactol Methyl Acetal (Rosuvastatin Lactol-OMe) a Compound of Formula 5 where $R^1$=iPr, $R^2$=4-FC₆H₄, $R^3$=Me, $R^4$=SO₂Me, $P^1$=H and W=—OP², in which $P^2$=Me Pyrimidyl-ethenyl-OH-lactol methyl acetal may be obtained by reaction of Pyrimidyl-ethenyl-O-benzyl-lactol methyl acetal with TMSI.

EXAMPLE 7

Preparation of Pyrimidyl-ethenyl-OH-lactol (Rosuvastatin Lactol), a Compound of Formula 5 where $R^1$=iPr, $R^2$=4-FC₆H₄, $R^3$=Me, $R^4$=SO₂Me, $P^1$=H and W=—OP², in which $P^2$=H Pyrimidyl-ethenyl-OH-lactol may be obtained by treatment of the Pyrimidyl-ethenyl-OH-lactol methyl acetal with 0.1 N HCl in methanol.

EXAMPLE 8

Preparation of Lactone, a Compound of Formula 6 where $R^1$=iPr, $R^2$-4-FC₆H₄, $R^3$=Me, $R^4$=SO₂Me, $P^1$=H The pyrimidyl-ethenyl-OH-lactol (35 mg, 0.065 mmol) in dichloromethane (0.5 ml) was added to Dess-Martin periodinane (30 mg, 0.07 mmol) and stirred at room temperature for 2.5 hours. The reaction was partitioned between 1M sodium hydroxide and diethyl ether. The phases were then separated and the organic volume reduced in vaccuo to afford the crude product oil.

EXAMPLE 9

Preparation of Rosuvastatin (Hydrolysis of Lactone), a Compound of Formula 7 where $R^1$=iPr, $R^2$=4-FC₆H₄, $R^3$=Me, $R^4$=SO₂Me The lactone (1.1 g) was dissolved in ethanol (10 ml). Water (2 ml) and Ca(OH)₂ (0.15 g) were added and the suspension warmed to 60° C. for 3 hours. A further 10 ml of warm water was added, then the mixture allowed to cool slowly to room temperature. The precipitate formed was filtered and dried to give Rosuvastatin calcium salt. The material was identical to an authentic sample by mixed melting point, NMR and mass spectrometry.

The invention claimed is:

1. A process for the preparation of a compound of formula (7):

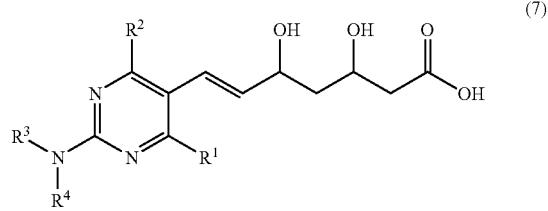

wherein $R^1$ represents an isopropyl group;

$R^2$ represents a 4-fluorophenyl group;

$R^3$ represents a methyl group; and $R^4$ represents a SO₂R⁵ group where $R^5$ is a methyl group, comprising the steps of:

a) hydroxylating a compound of formula (1):

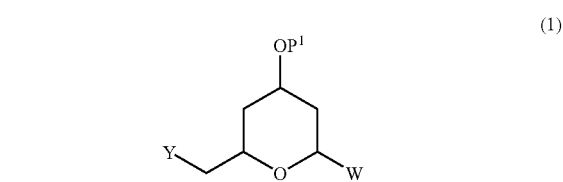

wherein Y represents a halo group; $P^1$ represents hydrogen or a protecting group selected from the group consisting of benzyl, benzoyl, methyl, silyl, and tetrahydropyranyl; and W represents —OP², in which $P^2$ represents a protecting group selected from the group consisting of benzyl, benzoyl, methyl, silyl, and tetrahydropyranyl, to give a compound of formula (2):

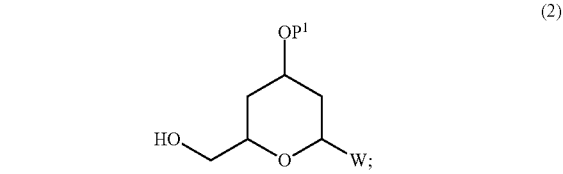

b) oxidising the compound of formula (2) to give a compound of formula (3):

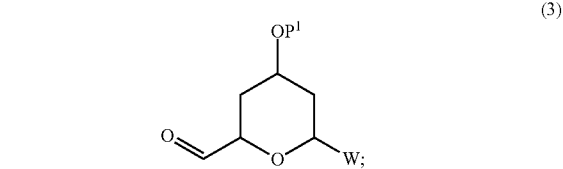

c) coupling the compound of formula (3) with a compound of formula (4):

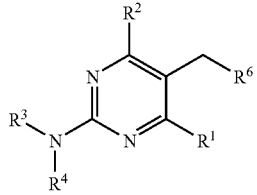
(4)

wherein $R^1$ represents an isopropyl group; $R^2$ represents a 4-fluorophenyl group; $R^3$ represents a methyl group; $R^4$ represents $SO_2R^5$ group where $R^5$ is a methyl group; and $R^6$ represents $P(=O)R^7R^8$ in which $R^7$ and $R^8$ each independently is a $C_{1-6}$ alkyl, $C_{6-12}$ aryl, $C_{1-6}$ alkoxy, or $C_{6-12}$ aryloxy group, to give a compound of formula (5):

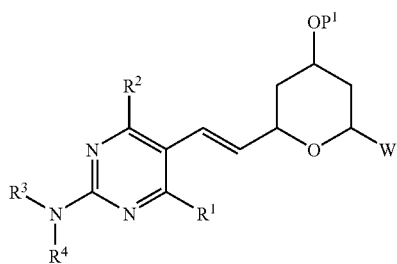
(5)

wherein $R^3$ represents a methyl group; and $R^4$ represents a $SO_2R^5$ group where $R^5$ is methyl group;

d) removing the $P^2$ protecting group and oxidising the compound of formula (5) to give a compound of formula (6):

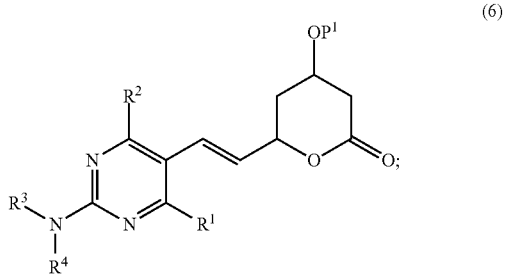
(6)

and e) subjecting the compound of formula (6) to ring-opening and removing any $P^1$ protecting group, to give a compound of formula (7).

2. The process of claim 1, wherein Y represents independently for each occurrence Cl or Br.

3. The process of claim 1, wherein $P^1$ represents benzyl, benzoyl, methyl, or silyl.

4. The process of claim 1, wherein $P^1$ represents benzyl or benzoyl.

5. The process of claim 1, wherein $P^1$ represents a trialkylsilyl or a triarylsilyl.

6. The process of claim 1, wherein $P^1$ represents a silyl selected from the group consisting of trimethylsilyl, tert-butyldimethylsilyl, and tert-butyldiphenylsilyl.

7. The process of claim 1, wherein $P^2$ represents benzyl.

8. The process of claim 1, wherein $P^2$ represents methyl.

9. The process of claim 1, wherein $R^7$ and $R^8$ are each independently a $C_{6-12}$ aryloxy group.

10. The process of claim 1, wherein $R^7$ and $R^8$ each independently is methyl, ethyl, phenyl, tolyl, naphthyl, methoxy, ethoxy or phenoxy.

11. The process of claim 1, wherein $R^7$ and $R^8$ represent phenoxy.

12. The process of claim 1, wherein $P^1$ represents benzyl or benzoyl; and $R^7$ and $R^8$ represent phenoxy.

* * * * *